(12) United States Patent
Malik et al.

(10) Patent No.: US 11,730,512 B2
(45) Date of Patent: Aug. 22, 2023

(54) LOCKING ASSEMBLY FOR MEDICAL DEVICE

(71) Applicant: Boston Scientific Limited, St. Michael (BB)

(72) Inventors: Sumit Malik, Haryana (IN); Salman Kapadia, Madhya Pradesh (IN)

(73) Assignee: Boston Scientific Limited, St. Michael (BB)

( * ) Notice: Subject to any disclaimer, the term of this patent is extended or adjusted under 35 U.S.C. 154(b) by 173 days.

(21) Appl. No.: 16/159,228

(22) Filed: Oct. 12, 2018

(65) Prior Publication Data

US 2019/0110810 A1 Apr. 18, 2019

Related U.S. Application Data

(60) Provisional application No. 62/571,685, filed on Oct. 12, 2017.

(51) Int. Cl.
*A61B 17/32* (2006.01)
*A61B 17/34* (2006.01)
(Continued)

(52) U.S. Cl.
CPC .......... *A61B 17/3403* (2013.01); *A61B 17/22* (2013.01); *A61B 17/3417* (2013.01);
(Continued)

(58) Field of Classification Search
CPC ........ A61B 2017/347; A61B 2090/034; A61B 2090/035; A61B 10/0275; A61B 17/3421; A61M 25/0606; A61M 25/0102; A61M 2025/09125; A61M 2025/0063; A61M 39/1011
See application file for complete search history.

(56) References Cited

U.S. PATENT DOCUMENTS

| 5,336,191 A | 8/1994 | Davis et al. | |
| 5,391,152 A * | 2/1995 | Patterson | ......... A61M 25/0097 604/533 |

(Continued)

FOREIGN PATENT DOCUMENTS

| CN | 104602625 A | 5/2015 |
| EP | 1 661 521 | 5/2006 |

(Continued)

OTHER PUBLICATIONS

International Search Report and Written Opinion issued in International Application No. PCT/IB2018/001268, dated Feb. 12, 2019 (13 pages).

(Continued)

*Primary Examiner* — Nathan R Price
*Assistant Examiner* — Tania Ismail
(74) *Attorney, Agent, or Firm* — Bookoff McAndrews, PLLC

(57) ABSTRACT

A medical device assembly may include a stylet having a distal stylet body and a proximal stylet hub, a cannula having a distal cannula body and a proximal cannula hub, and a lock for securing the stylet to the cannula, wherein the lock includes at least one abutment on at least one of the stylet hub and the cannula hub for restricting relative movement between the stylet hub and the cannula hub.

19 Claims, 3 Drawing Sheets

(51) Int. Cl.
*A61B 90/00* (2016.01)
*A61B 17/22* (2006.01)
*A61M 39/10* (2006.01)
*A61B 17/00* (2006.01)
*A61M 25/09* (2006.01)
*A61B 10/02* (2006.01)
*A61M 25/06* (2006.01)
*A61M 25/00* (2006.01)
*A61M 25/01* (2006.01)
*A61B 1/313* (2006.01)

(52) U.S. Cl.
CPC .......... *A61B 17/3421* (2013.01); *A61B 90/03* (2016.02); *A61M 39/1011* (2013.01); *A61B 1/313* (2013.01); *A61B 10/0275* (2013.01); *A61B 2017/00477* (2013.01); *A61B 2017/347* (2013.01); *A61B 2090/034* (2016.02); *A61B 2090/035* (2016.02); *A61M 25/0102* (2013.01); *A61M 25/0606* (2013.01); *A61M 2025/0063* (2013.01); *A61M 2025/09125* (2013.01); *A61M 2039/1027* (2013.01)

(56) References Cited

U.S. PATENT DOCUMENTS

| | | | | |
|---|---|---|---|---|
| 5,885,217 | A | * | 3/1999 | Gisselberg ........ A61M 25/0606 604/164.04 |
| 10,588,660 | B2 | * | 3/2020 | Brockman ......... A61B 17/3421 |
| 2015/0201963 | A1 | | 7/2015 | Snow |
| 2016/0331929 | A1 | | 11/2016 | Lampropoulos et al. |

FOREIGN PATENT DOCUMENTS

| | | |
|---|---|---|
| EP | 2 486 880 | 8/2012 |
| WO | WO 2009/067661 | 5/2009 |

OTHER PUBLICATIONS

Office Action in Chinese Patent Application No. 201880064501.2, dated Nov. 1, 2022 (8 pages).

\* cited by examiner

LOCKING ASSEMBLY FOR MEDICAL DEVICE

CROSS-REFERENCE TO RELATED APPLICATIONS

This patent application claims the benefit of priority under 35 U.S.C. § 119 to U.S. Provisional Patent Application No. 62/571,685, filed Oct. 12, 2017, which is herein incorporated by reference in its entirety.

TECHNICAL FIELD

Aspects of the present disclosure generally relate to medical devices and procedures. In particular, aspects of this disclosure relate to coupling mechanisms and associated methods for medical devices.

INTRODUCTION

Non-invasive surgical procedures enable a medical professional to treat an internal area of a body while minimizing a size of a physical opening in the exterior skin of the body. Many non-invasive surgical procedures are design to treat a particular area of the body, such as a specific organ. Percutaneous nephrolithotomy ("PCNL") is a reliable minimally-invasive approach for managing kidney stones. PCNL may be used to remove a kidney stone positioned in a body where other (e.g., ureteroscopic) approaches would be less effective. For example, PCNL may be the preferred method for treating: staghorn calculi or large (e.g., greater than 2 cm) intrarenal stones; stones with concomitant ureteropelvic junction obstruction; and/or intrarenal stones not amenable to extracorporeal shockwave lithotripsy ("SWL") or endoscopic management due to stone composition or anatomic variability.

In some PCNL procedures, a needle is inserted through the body and into a kidney for management of the kidney stones. Precise placement of the needle is necessary for ensuring a successful and complication-free PCNL procedure. A medical professional needs to have detailed understanding of the anatomy in and around the kidney to be able to visualize the kidney and surrounding tissues when making a puncture through the skin. Accordingly, the step of gaining access to the kidney via a puncture through the skin may necessitate a medical professional having significant experience and/or the assistance of a radiologist to ensure the accurate location and angle of access to the kidney through the puncture in the skin. These efforts may consume operating time and expose the patient to higher amounts of radiation.

Commonly used PCNL access needles comprise a stylet and a cannula. The stylet has a sharp tip and is used to provide access to the kidney, and the cannula serves as sheath for the stylet and provides an access channel to the kidney. During insertion of the stylet and cannula, the stylet can pop out of the cannula due to axial or other forces from the patient's body, creating difficulty in advancing the access system to the desired location.

The mechanisms and methods described herein are provided to rectify deficiencies described in conventional designs and offer improvements that may help address other problems.

SUMMARY

Aspects of the present disclosure relate to, among other things, medical device assemblies and locking assemblies. Each of the aspects disclosed herein may include one or more of the features described in connection with any of the other disclosed aspects.

In one example, a medical device assembly may include a stylet having a distal stylet body and a proximal stylet hub, a cannula having a distal cannula body and a proximal cannula hub, and a lock for securing the stylet to the cannula. The lock of the medical device assembly may include at least one abutment on at least one of the stylet hub and the cannula hub, for restricting relative movement between the stylet hub and the cannula hub.

Examples of the medical device assembly may include one or more of the following features. The lock may include one of a protrusion or a channel on the stylet hub configured to engage with one of a channel or protrusion on the cannula hub. A distal surface of the stylet hub may contact a proximal surface of the cannula hub when the medical device assembly is in a locked configuration. The lock may include a protrusion on the stylet hub and a channel on the cannula hub, and the protrusion may be received within the channel when the medical device assembly is in a locked configuration and at least one abutment is on at least one of the protrusion or the channel. The lock may include a projection with threads on the cannula hub configured to engage with complimentary threads on the stylet hub. A generally planar distal surface of the stylet hub may abut a generally planar proximal surface of the cannula hub when the medical device assembly is in the locked configuration. The stylet may protrude from a distal portion of the cannula when the medical device assembly is in the locked configuration.

In a further example, a medical device assembly may include a stylet having a stylet body and a stylet hub. The stylet hub may include two clasp arms, and each clasp arm may include an anchor. The medical device assembly may also include a cannula having a cannula body and a cannula hub. The cannula hub may include a locking protrusion. A proximal surface of each anchor of the clasp arms may be in contact with the locking protrusion in a locked configuration of the stylet and the cannula to restrict withdrawal of one of the stylet hub and the cannula hub from the other of the stylet hub and the cannula hub.

In addition, examples of the medical device assembly may include one or more of the following features. A proximal surface of each anchor of the clasp arms may not be in contact with the locking protrusion in an unlocked configuration of the stylet and the cannula. Each clasp arm may be coupled to a hinge. Each clasp arm may include a recess. The locking protrusion may be received within each recess when the medical device assembly is in the locked configuration. Each clasp arm may include a curvature at a proximal portion of the clasp arm. Each clasp arm may be biased in a radially inward direction towards the central longitudinal axis of the stylet. The clasp arms may be the distalmost portions of the stylet hub. Each clasp arm may include gripping ridges on a proximal surface of each clasp arm. A proximal portion of the cannula hub may be within the stylet hub when the medical device assembly is in the locked configuration.

In another example, a locking assembly may include a stylet hub including a protrusion and a cannula hub including a recess. The protrusion may slide into the recess when the locking assembly is in a locked configuration. The stylet hub may include a recess including threads. The cannula hub may include a projection including threads complimentary to the threads of the stylet hub. The projection of the cannula hub may be within the recess of the stylet hub when the locking assembly is in the locked configuration.

BRIEF DESCRIPTION OF THE DRAWINGS

The accompanying drawings, which are incorporated in and constitute a part of this specification, illustrate various aspects and together with the description, serve to explain the principles of the disclosed aspects.

DETAILED DESCRIPTION

Reference will now be made in detail to aspects of the present disclosure, which are illustrated in the accompanying drawings. Wherever possible, the same reference numbers will be used throughout the drawings to refer to the same or like parts or components. The term "distal" refers to the direction that is away from the user or operator and into the patient's body. By contrast, the term "proximal" refers to the direction that is closer to the user or operator and away from the patient's body. Unless stated otherwise, terms such as "generally," "about," "substantially," and/or "approximately" indicate a range of possible values that are within +/−5% of a stated value or condition.

Aspects of the present disclosure are directed to medical devices configured to pass a medical device assembly through the body of a patient. For example, aspects of the present disclosure may relate to medical systems, devices, and methods for inserting a medical device assembly comprising a stylet and a cannula through a patient during a medical procedure, such as, for example, a procedure to remove kidney stones or other material from a patient's kidney or other organ. In some aspects, for example, the medical systems of the present disclosure may include a needle assembly with a stylet, a cannula, and a locking mechanism locking the stylet to the cannula.

Figure 1A:
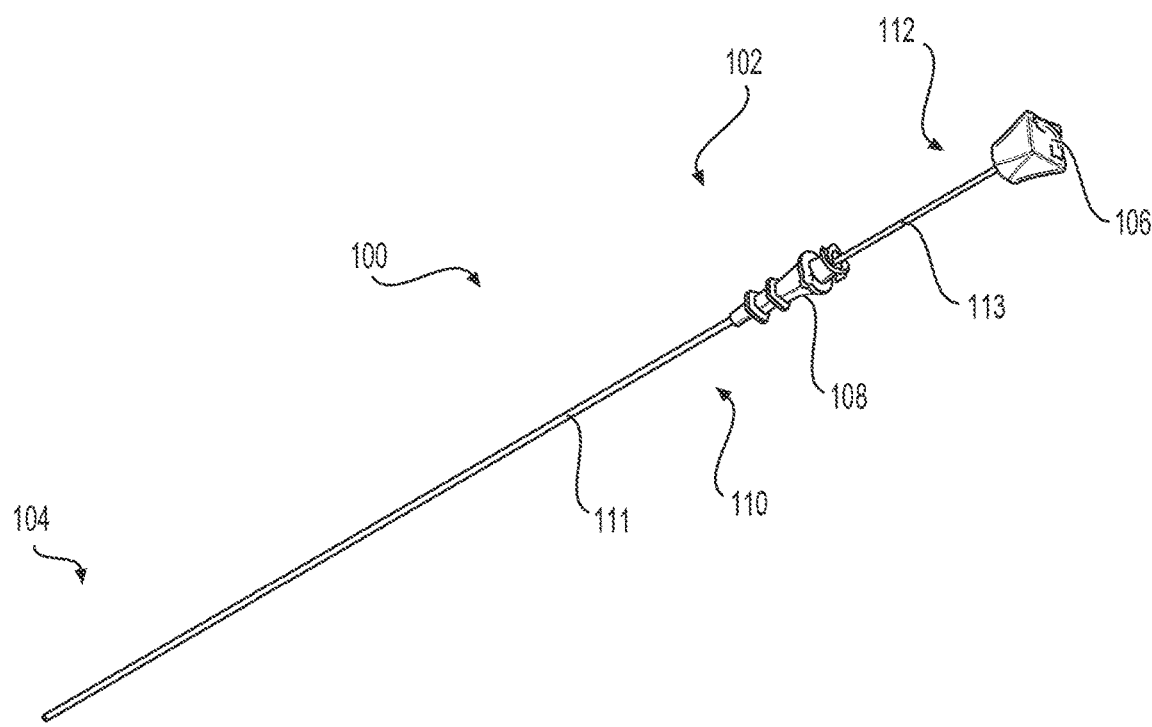
FIGS. 1A and 1B illustrate perspective views of a medical device assembly, according to an aspect of the present disclosure.
Figure 1B:
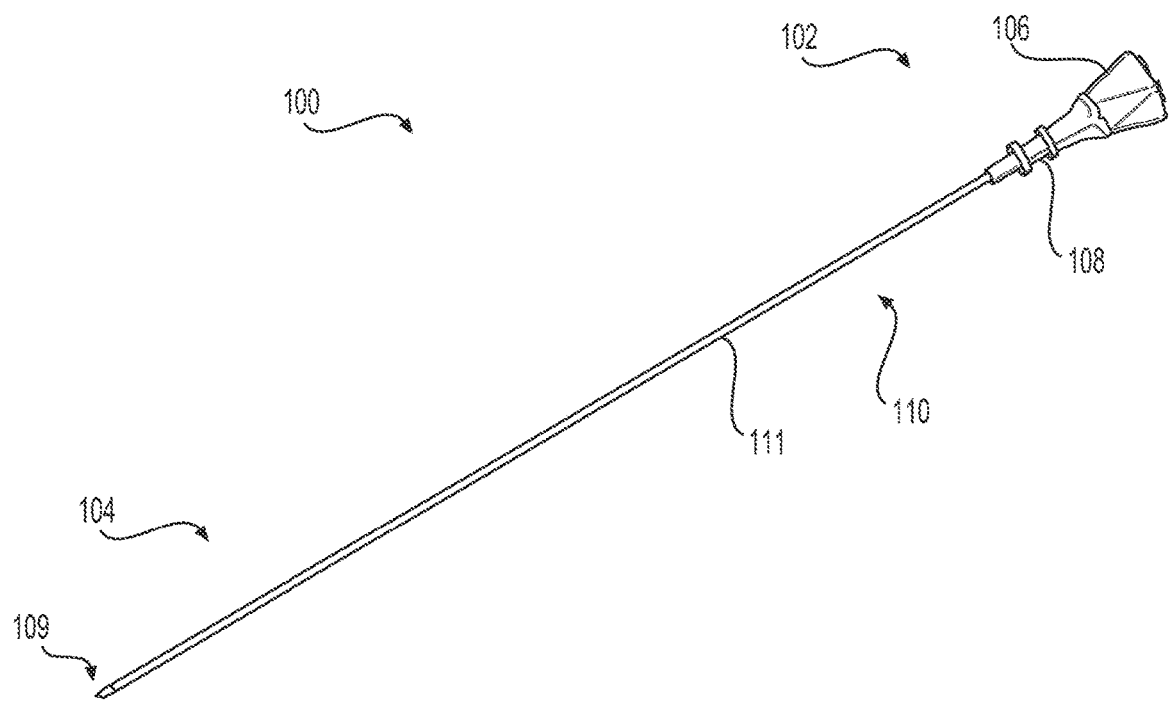

FIGS. 1A and 1B illustrate an example of a medical device assembly 100 including a stylet 112 and a cannula 110. Stylet 112 may have a stylet hub 106 and a stylet body 113, and cannula 110 may have a cannula hub 108 and a cannula body 111. Stylet body 113 may have a sharp tip 109. Medical device assembly 100 is shown in a first, unlocked configuration in FIG. 1A, and in a second, locked configuration in FIG. 1B. Medical device assembly 100 may extend longitudinally from a proximal end 102 toward a distal end 104. Stylet 112 may be cylindrical, although any geometric shape may be used; may extend longitudinally in the proximal-distal direction; and may have a sharp point present at its distal tip. In some aspects, stylet 112 and/or stylet body 113 may be a needle.

Cannula 110 may be cylindrical, although any geometric shape that may receive stylet 112 may be used, and may also extend longitudinally in the proximal-distal direction. A lumen may run longitudinally through cannula 110 and may be configured to received stylet 112.

In the locked configuration (shown in FIG. 1B), stylet 112 may be partially encased within cannula 110 and may be partially exposed outside cannula 110 at a distal portion of stylet 112. Stylet hub 106 may be coupled to cannula hub 108 in the locked configuration and may be separated from cannula hub 108 in the unlocked configuration. Stylet hub 106 is fixedly secured to a proximal end portion of stylet body 113. Similarly, cannula hub 108 is fixedly secured to a proximal end portion of cannula body 111. Cannula hub 108 includes a proximal opening configured to receive stylet 112 for insertion of stylet body 113 into the lumen of cannula 110.

Figure 2A:
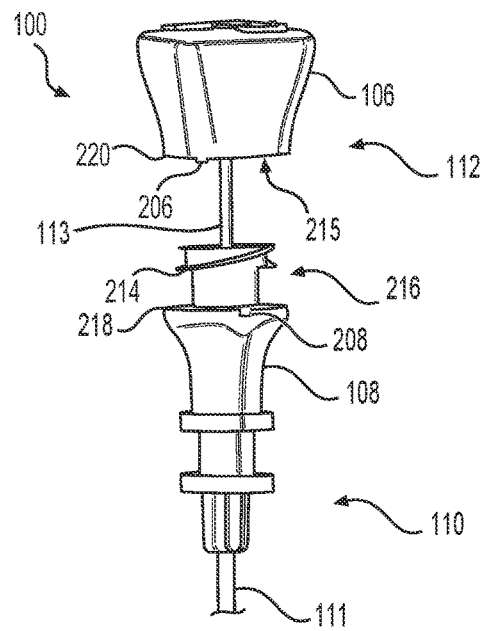
FIGS. 2A and 2B illustrate perspective views of a proximal section of the medical device assembly of FIGS. 1A and 1B, according to an aspect of the present disclosure.
Figure 2B:
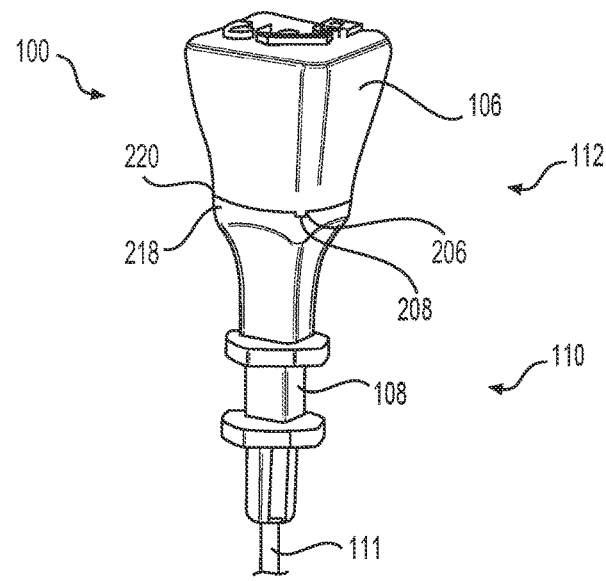

FIGS. 2A and 2B show perspective views of a proximal portion of the medical device assembly 100 in FIGS. 1A and 1B, including stylet 112, stylet hub 106, stylet body 113, cannula 110, cannula body 111 and cannula hub 108. Medical device assembly 100 is shown in an unlocked configuration (FIG. 2A) and a locked configuration (FIG. 2B).

Stylet 112, stylet hub 106, stylet body 113, cannula 110, cannula hub 108, and cannula body 111 may be made of any suitable material, such as metal, plastic, polymer, etc. Stylet hub 106 may be rectangular and may taper in the proximal-distal direction. In other aspects, stylet hub 106 may be circular, pyramidal, pentagonal, or any other shape. Stylet hub 106 may have a generally planar distal surface 220 including a distal protrusion 206 extending distally from the distal surface 220 of stylet hub 106. Distal protrusion 206 may extend parallel to the longitudinal axis of stylet 112 and/or stylet body 113. In other aspects, distal surface 220 may include a channel or recess (not shown) extending proximally from distal surface 220. Stylet hub 106 may include a hollow portion or recess 215 running longitudinally in the distal-proximal direction from distal surface 220, and the recess may include female threads configured to receive male threads present on the cannula hub 108. In other aspects, the recess may include male threads configured to fit into female threads present on the cannula hub 108.

Cannula hub 108 may have an outer rectangular shape and may taper in the proximal-distal direction. In some aspects, cannula hub 108 may be circular, pyramidal, pentagonal, or any other shape. Cannula hub 108 may include a generally planar proximal surface 218 at a proximal portion of the cannula hub 108. Proximal surface 218 may be configured to align with distal surface 220 of the stylet hub 106 when medical device assembly 100 is in a locked position. The proximal surface 218 may include a recess or channel 208 which may extend in a distal direction (FIG. 2B). Channel 208 may be configured to receive protrusion 206 of stylet hub 106. In other aspects, proximal surface 218 may include a protrusion (not shown) extending in the proximal direction from proximal surface 218, and the protrusion may be configured to extend into a channel or recess present on the distal surface 220 of stylet hub 106. Cannula hub 108 may include a proximal projection or stem 216 including threads 214 extending proximally from the proximal surface 218. The proximal projection 216 may be configured for insertion into the recess 215 in stylet hub 106, and threads 214 (male or female) of the proximal projection 216 may align with threads (female or male) present on the stylet hub 106 (e.g., in recess 215).

Stylet 112 may be pushed distally into the cannula hub 108 and into cannula body 111 along its longitudinal axis. After inserting a portion of stylet 112 into cannula 110, stylet hub 106 may contact cannula hub 108 and threads 214 of cannula hub 108 may engage threads present on stylet hub 106. After engagement with cannula hub 108, stylet hub 106 threads are rotated over the cannula hub 108 threads 214 and the projection 216 of cannula hub 108 is inserted into the recess 215 in stylet hub 106.

When stylet hub 106 is engaged with cannula hub 108, rotating stylet hub 106 may move distal surface 220 towards or away from proximal surface 218 of cannula hub 108 depending on the direction of rotation. After a specific amount of relative rotation between stylet hub 106 and cannula hub 108, protrusion 206 of stylet hub 106 engages with and/or is inserted into, snaps, or otherwise fits into channel 208 of cannula hub 108, facilitating the rotational locking of stylet hub 106 to cannula hub 108. In some aspects, protrusion 206 of stylet hub 106 engages with and/or is inserted into channel 208 after less than 90 degrees of relative rotation of stylet hub 106 and cannula hub 108. In other aspects, protrusion 206 may engage channel 208 after relative rotation of 45 degrees, 130 degrees, 180 degrees or any other degree of rotation. Stylet 112, including stylet body 113 and stylet hub 106, may be locked to cannula 110, including cannula hub 108 and cannula body 111, when protrusion 206 is inserted into channel 208, such that stylet 112 and cannula 110 move as a singular unit. FIG. 2B shows stylet hub 106 and cannula hub 108 in a locked configuration with protrusion 206 inserted into channel 208. In a locked configuration, distal surface 220 of stylet hub 106 may be flush or align with proximal surface 218 of cannula hub 108. To unlock stylet 112 from cannula 110 in medical device assembly 100, the user may rotate stylet hub 106 and/or cannula hub 108 in the direction opposite the direction used to lock medical device assembly 100.

In some aspects, medical device assembly 100 may provide tactile or audible feedback when protrusion 206 is inserted into channel 208 and/or stylet hub 106 is locked to cannula hub 108. For example, medical device assembly 100 may make an audible snapping or clicking sound when stylet hub 106 and cannula hub 108 are locked together as one or more surfaces of protrusion 206 rapidly moves into contact with one or more surfaces of channel 208. This may be caused by protrusion 206 being compressed against proximal surface 218 during turning of stylet hub 106, as protrusion 206 slides across proximal surface 218, and protrusion 206 expands from its compressed state into channel 208. Once in the locked configuration (shown in FIG. 2B), medical device assembly 100 prevents stylet 113 from extending out of or "popping" out of cannula 110 while a user is manipulating the medical device assembly 100, such as while a distal portion of medical device assembly 100 is being inserted in to a patient.

Figure 3A:
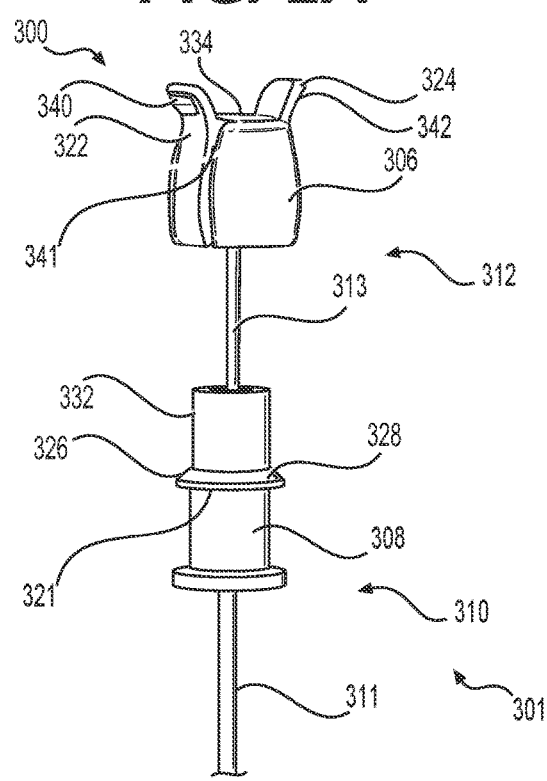
FIGS. 3A and 3B illustrate perspective views of a proximal section of a medical device assembly, according to another aspect of the present disclosure.
Figure 3B:
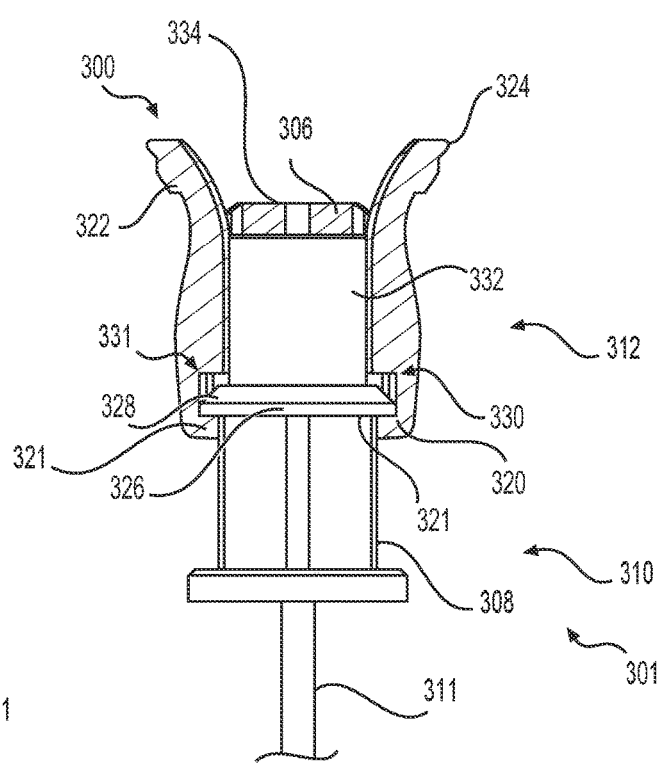

FIGS. 3A and 3B illustrate a perspective view and a cross-sectional view, respectively, of a proximal portion of an exemplary medical device assembly 300, including locking assembly 301, according to another aspect of the present disclosure. Medical device assembly 300 may include a stylet 312, stylet hub 306, stylet body 313, cannula 310, cannula hub 308, and cannula body 311, and each of these components may have any of the features previously described in relation to medical device assembly 100. Medical device assembly 300 is shown in an unlocked configuration (FIG. 3A) and a locked configuration (FIG. 3B).

Cannula hub 308 may be cylindrical and may include a locking protrusion 326 which protrudes radially outward from the longitudinal axis of the cannula 310 and may form a ring around cannula hub 308. Locking protrusion 326 may include an angular sidewall 328 which may face the proximal direction and may taper the locking protrusion 326. Proximal portion 332 of cannula hub 308 may be configured to fit within stylet hub 306. Locking protrusion 326 may include a planar distal surface 321.

Stylet hub 306 may comprise clasp arms 322, 324 along a radial sidewall of the stylet hub 302. Clasp arms 322, 324 may be on opposite sides of stylet hub 306, and a cylindrical body of stylet hub 306 may be between clasp arms 322, 324. Stylet hub 306 may further comprise a top surface 334, hinges 341, proximal end portions 340, 342 of clasp arms 322, 324. Clasp arms 322, 324 may be substantially parallel to stylet body 313 and/or may extend longitudinally in the proximal-distal direction. Clasp arms 322, 324 may include proximal end portions 340, 342 extending proximally above a top surface 334 of stylet hub 302. In some aspects, the proximal end portions 340, 342 may curve outward from the longitudinal axis of stylet 312, and in other aspects proximal end portions 340, 342 may be straight. Each clasp arm 322, 324 may include locking anchors 320, 321 including recesses 330, 331 (shown in FIG. 3B) located at a distal end section of each clasp arm 322, 324. Recesses 330, 331 may be configured to receive locking protrusion 326. Clasp arms 322, 324 may be coupled to stylet hub 302 via hinges 341. Hinges 341 may be living hinges and may be located at a proximal section of each clasp arm 322, 324. Alternatively, hinges 341 may include cylindrical protrusions on claps arms 322, 324 that are rotatably received in cylindrical recesses in stylet hub 306, or vice versa. Clasp arms 322, 324 provide a user with a means to lock and unlock the medical device assembly with a single hand.

Stylet hub 306 and cannula hub 308 may be used to couple stylet 312 to cannula 310. To lock together stylet 312 and cannula 310, first, stylet 312 is inserted into cannula 310 and stylet hub 306 is pushed towards cannula hub 308. Then, as the user continues to insert stylet 312 into cannula 310, locking anchors 320, 321 of clasp arms 322, 324 engage locking protrusion 326 and slide over angular sidewall 328, which may cause locking anchors 320, 321 to move radially outward. Locking protrusion 326 is inserted into recess portion 330, 331 of each clasp arm 322, 324 as locking anchors 320, 321 move radially inward. Clasp arms 322, 324 may rotate or pivot about their hinges 341 and may be biased (e.g., spring-biased) to move the locking anchors 320, 321, radially inward towards the longitudinal axis of stylet 312 and cannula 310. Once locking protrusion 326 is inserted into each recess 330, 331 stylet 312 and cannula 310 are locked or coupled together.

In some aspects, locking assembly 301 may provide tactile or audible feedback when locking protrusion 326 is inserted into each recess 330, 331. For example, locking assembly 301 may make an audible snapping or clicking sound when locking protrusion 326 is inserted into each recess 330, 331. The sound may be generated as the biasing forces locking anchors 320, 321 back into contact with the cannula hub 308 after having been pushed apart.

To unlock stylet 312 from cannula 310 of medical device assembly 300, the user may press on proximal end portions 340, 342 of each clasp arm 322, 324, in the radially inward direction towards the central longitudinal axis of stylet 312. By pressing on proximal end portions 340, 342 of each clasp arm 322, 324, the clasp arms may rotate or pivot about their hinges and release each locking anchor 320, 321 from locking protrusion 326, removing locking protrusion 326 from each recess 330, 331. While exerting force on proximal end portions 340, 342 of clasp arms 322, 324, the user may then pull or translate stylet hub 306 in the proximal direction to remove stylet 312 from cannula 310. The amount of force that is exerted on proximal end portions 340, 342 may vary with the dimension, positioning and shape of the hinges and/or clasp arms, such as a square or circular hinge.

Figure 4A:
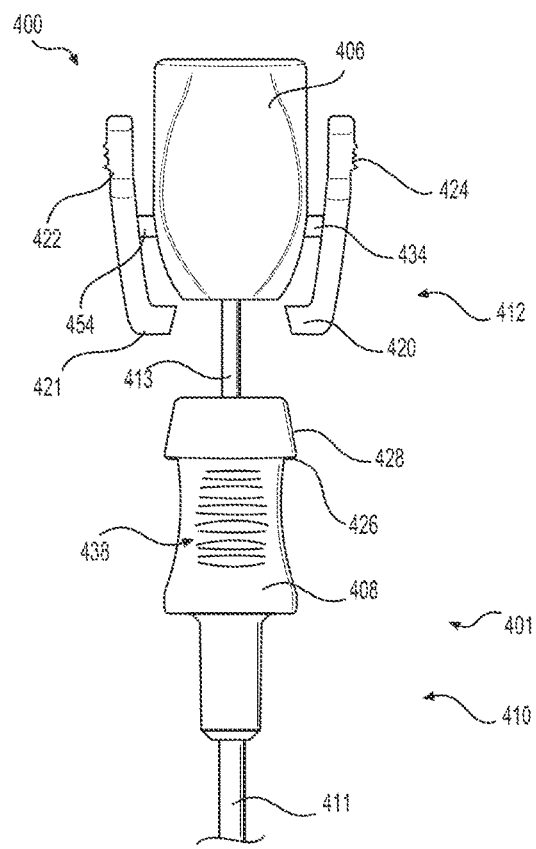
FIGS. 4A and 4B illustrate perspective views of a proximal section of a medical device assembly, according to yet another aspect of the present disclosure.
Figure 4B:
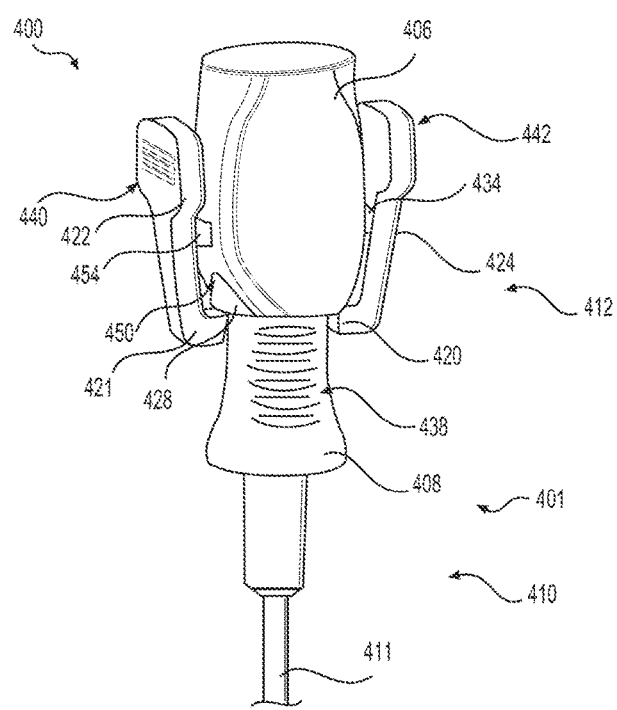

FIGS. 4A and 4B illustrate perspective views of a proximal portion of another exemplary medical device assembly 400, including locking assembly 401. Medical device assembly 400 is substantially similar to medical device assembly 300, including stylet 412, stylet hub 406, stylet body 413, cannula 410, cannula hub 408, cannula body 411, clasp arms 422, 424, hinges 434, 454, locking protrusion 428, and proximal end portions 440, 442. Cannula hub 404 may include ridges 438 to enhance a user's grip of cannula hub 404. Hinges 434, 454 of stylet hub 406 may be square shaped (shown in FIG. 4A) and clasp arms may include locking anchors 420, 421. Clasp arms 422, 424 may be configured to receive locking protrusion 428 at a proximal surface of locking anchors 420, 421.

A user may lock stylet 412 to cannula 410 using medical device assembly 400 in substantially the same manner as locking assembly 301. Locking protrusion 428 may engage locking anchors 420, 421 of clasp arms 422, 424, and may spread locking anchors 420, 421 apart. Locking protrusion 428 may be inserted further within stylet hub 406 to a locked position (shown in FIG. 4B), when a biasing force returns locking anchors 420, 421 to their radially inward positions such that locking anchors 420, 421 may block withdrawal of locking protrusion 428 from stylet hub 406. A distal portion of stylet hub 406 may include a curvature 450 to facilitate the insertion of locking protrusion 428 within stylet hub 406. The user may apply (and maintain) pressure to levers 440, 442 to release locking anchors 420, 421, unlock stylet 412 from cannula 410, and remove stylet 412 from cannula 410.

Any of the medical device assemblies described above may be utilized in any type of medical procedure. For example, a stylet may be locked to a cannula using any of the above-described locking assemblies prior to puncturing a patient using the stylet. In other aspects, a medical device assembly may be inserted into a patient's body through a lumen of a different medical device, such as an endoscope. A medical device assembly, including stylet, cannula, and a locking assembly, may be advanced towards a target area within the patient. After a distal section of the medical device assembly reaches the target area within the patient, the stylet may be unlocked from the cannula and removed from the patient, providing an access channel through the cannula to the target area of the patient. In some examples, the medical device assembly may be advanced through the body of a patient to a target area within a kidney.

Those skilled in the art will understand that the medical devices set out above can be implemented in any suitable procedure without departing from the scope of the disclosure as defined by the claims. In particular, constructional details, including manufacturing techniques and materials, are well within the understanding of those of skill in the art and have not been set out in any detail here. These and other modifications and variations are well within the scope of the present disclosure and can be envisioned and implemented by those of skill in the art.

Other aspects of the present disclosure will be apparent to those skilled in the art from consideration of the specification and practice of the aspects disclosed herein. It is intended that the specification and aspects be considered as implementations only, and departures in form and detail may be made without departing from the scope and spirit of the present disclosure as defined by the following claims.

What is claimed is:

1. A medical device assembly, comprising:
a stylet having a distal stylet body and a proximal stylet hub;
a cannula having a distal cannula body and a proximal cannula hub; and
a lock for securing the stylet to the cannula, wherein the lock includes at least one abutment on at least one of the stylet hub and the cannula hub, for restricting relative movement between the stylet hub and the cannula hub,
wherein a generally planar distal surface of the stylet hub abuts a generally planar proximal surface of the cannula hub when the medical device assembly is in a locked configuration, wherein each of the generally planar distal surface and the generally planar proximal surface is rectangular and includes corners,
wherein one of the proximal surface of the cannula hub and the distal surface of the stylet hub includes at least one channel configured to receive at least one protrusion extending from the other one of the distal surface of the stylet hub and the proximal surface of the cannula hub,
wherein the at least one protrusion is on at least one of the corners of the generally planar distal surface or at least one of the corners of the generally planar proximal surface, and the at least one channel is on at least one of the corners of the other one of the generally planar distal surface and the generally planar proximal surface,
wherein, in the locked configuration, the at least one protrusion is configured to disengage from the at least one channel via only relative rotation between the proximal stylet hub and the proximal cannula hub, and
wherein the at least one channel and the at least one protrusion both extend parallel to a longitudinal axis of the stylet.

2. The medical device assembly of claim 1, wherein:
the at least one protrusion is on the stylet hub;
the at least one channel is on the cannula hub; and
the at least one protrusion is received within the at least one channel when the medical device assembly is in a locked configuration, wherein the at least one abutment is on at least one of the at least one protrusion or the at least one channel.

3. The medical device assembly of claim 1, wherein the lock includes:
a projection with threads on the cannula hub configured to engage with complimentary threads on the stylet hub.

4. The medical device assembly of claim 1, wherein the stylet protrudes from a distal portion of the cannula when the medical device assembly is in the locked configuration.

5. A locking assembly, comprising:
a stylet hub including a protrusion; and
a cannula hub including a recess, wherein the protrusion is positioned in the recess when the locking assembly is in a locked configuration,
wherein a generally planar distalmost surface of the stylet hub abuts a generally planar proximal surface of the cannula hub when the locking assembly is in the locked configuration, wherein each of the generally planar distalmost surface and the generally planar proximal surface is rectangular and includes corners,
wherein the protrusion is on one of the corners of the generally planar distalmost surface, and the recess is on one of the corners of the generally planar proximal surface,
wherein a distalmost surface of the protrusion is flush against a proximal facing surface of the recess in the locked configuration, and
wherein the protrusion extends distally from the generally planar distalmost surface of the stylet hub and the recess extends distally from the generally planar proximal surface of the cannula hub, and wherein the recess is configured to receive the protrusion after relative rotation between the stylet hub and the cannula hub of approximately 130° or approximately 180°.

6. The locking assembly of claim 5, wherein:
the stylet hub further comprises a recess including threads,
the cannula hub further comprises a projection including threads complimentary to the threads of the stylet hub, and
the projection of the cannula hub is within the recess of the stylet hub when the locking assembly is in the locked configuration.

7. The medical device assembly of claim 1, wherein a distalmost surface of the stylet hub abuts a generally planar proximal surface of the cannula hub.

8. The medical device assembly of claim 2, wherein the channel receives the protrusion via relative rotation between the stylet hub and the cannula hub.

9. The medical device assembly of claim 1, wherein the medical device assembly provides tactile or audible feedback when the protrusion is received within the channel, and the medical device assembly transitions into a locked configuration.

10. The locking assembly of claim 5, wherein the protrusion is configured to audibly snap into the recess via relative rotation between the stylet hub and the cannula hub.

11. The locking assembly of claim 5, wherein, in the locked configuration, the protrusion is configured to disengage from the recess via relative rotation between the stylet hub and the cannula hub.

12. An assembly, comprising:
a stylet having a distal stylet body and a proximal stylet hub;
a cannula having a distal cannula body and a proximal cannula hub; and
wherein a generally planar distalmost surface of the stylet hub is flush against a planar proximal surface of the cannula hub when the assembly is in a locked configuration, wherein each of the generally planar distalmost surface and the generally planar proximal surface is rectangular and includes corners, and wherein:
one of the proximal surface of the cannula hub and the distal surface of the stylet hub includes at least one channel configured to receive at least one protrusion extending from the other one of the distal surface of the stylet hub and the proximal surface of the cannula hub, wherein the protrusion is on one of the corners of the generally planar distalmost surface, and the channel is on one of the corners of the generally planar proximal surface,
wherein the at least one channel receives the at least one protrusion via relative rotation between the stylet hub and the cannula hub,
wherein the at least one protrusion is configured to disengage from the at least one channel via only relative rotation between the stylet hub and the cannula hub,
wherein the at least one channel and the at least one protrusion both extend parallel to a longitudinal axis of the stylet, the at least one protrusion extends distally from the generally planar distalmost surface of the stylet hub, and the at least one channel extends distally from the generally planar proximal surface of the cannula hub, and
wherein the at least one channel receives the at least one protrusion after relative rotation between the stylet hub and the cannula hub of approximately 130° or approximately 180°.

13. The assembly of claim 12, wherein:
the stylet hub further comprises a recess including threads, and
the cannula hub further comprises a projection including threads complimentary to the threads of the stylet hub.

14. The assembly of claim 12, wherein in the locked configuration, a proximal portion of the stylet is partially encased within the cannula and a distal portion of the stylet is partially exposed outside the cannula.

15. The assembly of claim 12, wherein the at least one protrusion is configured to audibly slide into the at least one channel via relative rotation between the stylet hub and the cannula hub.

16. The medical device assembly of claim 1, wherein the generally planar distal surface is configured to move towards the generally planar proximal surface via a rotation of the proximal stylet hub relative to the proximal cannula hub in a first direction.

17. The medical device assembly of claim 16, wherein the generally planar distal surface is configured to move away from the generally planar proximal surface via a rotation of the proximal stylet hub relative to the proximal cannula hub in a second direction.

18. The medical device assembly of claim 1, wherein the at least one channel is configured to receive the at least one protrusion after relative rotation between the stylet hub and the cannula hub of approximately 130° or approximately 180°.

19. The assembly of claim 12, wherein the generally planar distalmost surface is configured to move towards or away from the generally planar proximal surface via a rotation of the proximal stylet hub relative to the proximal cannula hub.

* * * * *